US006975922B2

(12) United States Patent
Duncan et al.

(10) Patent No.: US 6,975,922 B2
(45) Date of Patent: Dec. 13, 2005

(54) SECURED DISPENSING CABINET AND METHODS

(75) Inventors: Mark Kevin Duncan, Redwood City, CA (US); Scott L. Kidney, Sunnyvale, CA (US); Brian R. Arnold, Aptos, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days.

(21) Appl. No.: 10/434,724

(22) Filed: May 8, 2003

(65) Prior Publication Data

US 2004/0225409 A1 Nov. 11, 2004

(51) Int. Cl.⁷ .............................................. G06F 17/00
(52) U.S. Cl. ......................... 700/242; 221/4; 221/241; 221/242
(58) Field of Search ..................... 700/242; 705/22, 705/23, 28, 29; 221/4, 241, 242

(56) References Cited

U.S. PATENT DOCUMENTS

| | | |
|---|---|---|
| 2,606,803 A | 8/1952 | Whelan |
| 2,653,850 A | 9/1953 | Vollten |
| 3,437,238 A | 4/1969 | Luba |
| 3,998,356 A | 12/1976 | Christensen |
| 4,062,385 A | 12/1977 | Katusha et al. |
| 4,225,056 A | 9/1980 | Flubacker |
| 4,267,942 A | 5/1981 | Wick, Jr. et al. |
| 4,360,125 A | 11/1982 | Martindale et al. |
| 4,482,233 A | 11/1984 | Bauer et al. |
| 4,519,522 A | 5/1985 | McElwee |
| 4,572,403 A | 2/1986 | Benaroya |
| 4,573,606 A | 3/1986 | Lewis et al. |
| 4,635,053 A | 1/1987 | Banks et al. |
| 4,663,621 A | 5/1987 | Field et al. |
| 4,695,954 A | 9/1987 | Rose et al. |
| 4,785,969 A | 11/1988 | McLaughlin |
| 4,811,764 A | 3/1989 | McLaughlin |
| 4,814,592 A | 3/1989 | Bradt et al. |
| 4,847,764 A | 7/1989 | Halvorson |
| 4,869,395 A | 9/1989 | Rubbmark |
| 4,915,571 A | 4/1990 | Toshihiko et al. |
| 4,967,928 A | 11/1990 | Carter |
| 4,995,498 A | 2/1991 | Menke |
| 5,190,185 A | 3/1993 | Blechl |
| 5,267,174 A | 11/1993 | Kaufman et al. |
| 5,377,864 A | 1/1995 | Blechl et al. |
| 5,419,410 A | 5/1995 | Yanagisawa |
| 5,745,366 A | 4/1998 | Higham et al. |
| 5,790,409 A | 8/1998 | Fedor et al. |
| 5,805,455 A | 9/1998 | Lipps |
| 5,805,456 A | 9/1998 | Higham et al. |
| 5,905,653 A | 5/1999 | Higham et al. |
| 5,927,540 A | 7/1999 | Godlewski |
| 6,039,467 A | 3/2000 | Holmes |
| 6,151,536 A | 11/2000 | Arnold et al. |
| 6,163,737 A | 12/2000 | Fedor et al. |
| 6,272,394 B1 | 8/2001 | Lipps |
| 6,471,089 B2 * | 10/2002 | Liff et al. ..................... 221/13 |
| 6,658,322 B1 * | 12/2003 | Frederick et al. ........... 700/236 |

* cited by examiner

Primary Examiner—Donald D. Walsh
Assistant Examiner—Jeffrey A. Shapiro
(74) Attorney, Agent, or Firm—Townsend and Townsend and Crew LLP

(57) ABSTRACT

A device for dispensing items comprises a cabinet having an interior for storing items. A dispenser frame is coupled to the cabinet and is configured to be accessed, such as by pulling the dispenser frame from the cabinet. The dispenser frame includes a plurality of dividers that are configured to hold the plurality of dispensing mechanisms that each hold multiple items within the storage area. Further, the dividers are reconfigurable to permit the arrangement of the dispensing mechanisms to be adjusted. A lockable door is coupled to the front of the cabinet in front of the dispenser frame. The door may be opened to provide access to the interior of the cabinet and to the dispenser frame. A dispense drawer is positioned below the storage area so that items dispensed from the dispensing mechanisms fall into the dispense drawer, where they may be accessed by pulling open the dispense drawer.

30 Claims, 13 Drawing Sheets

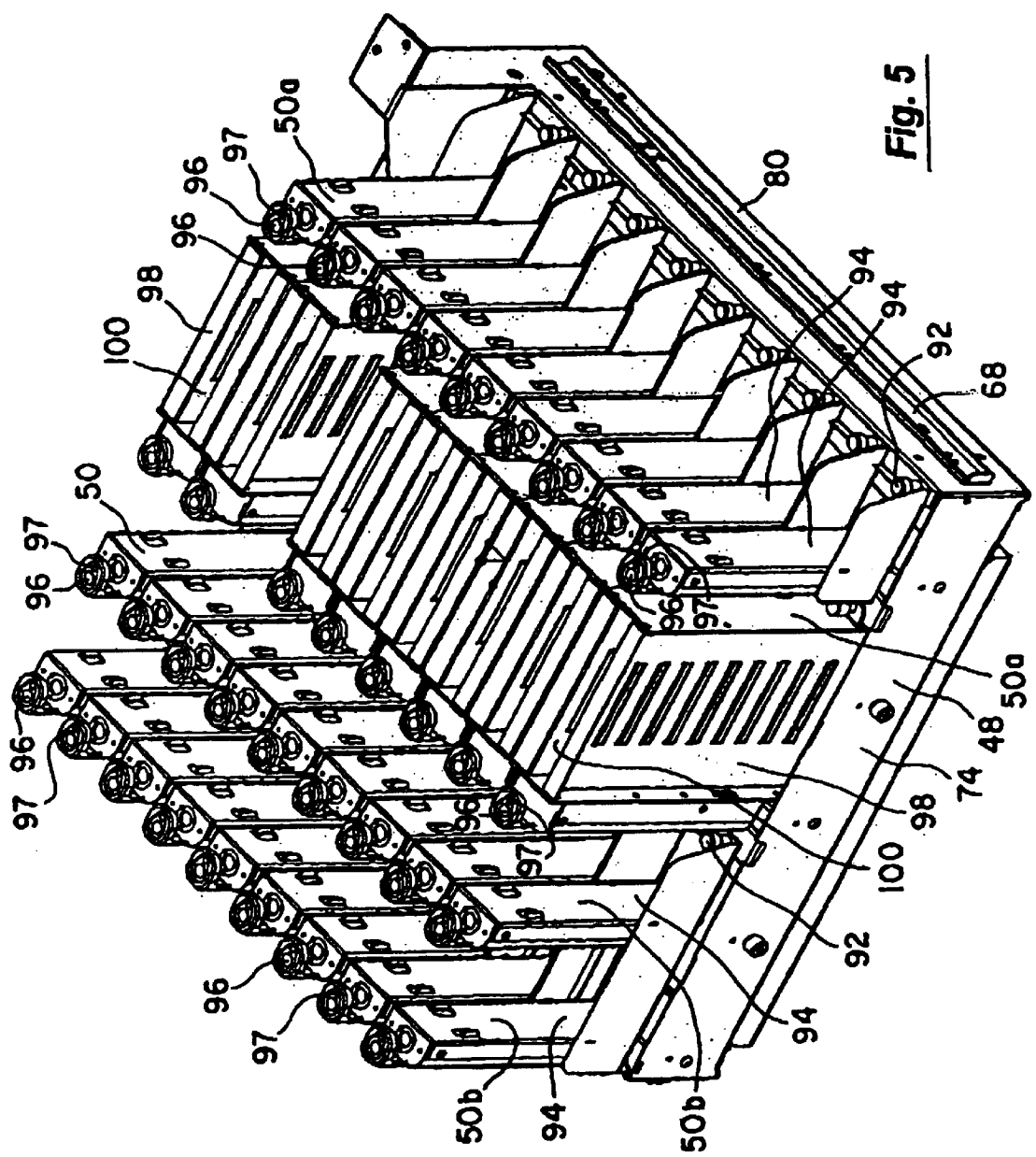

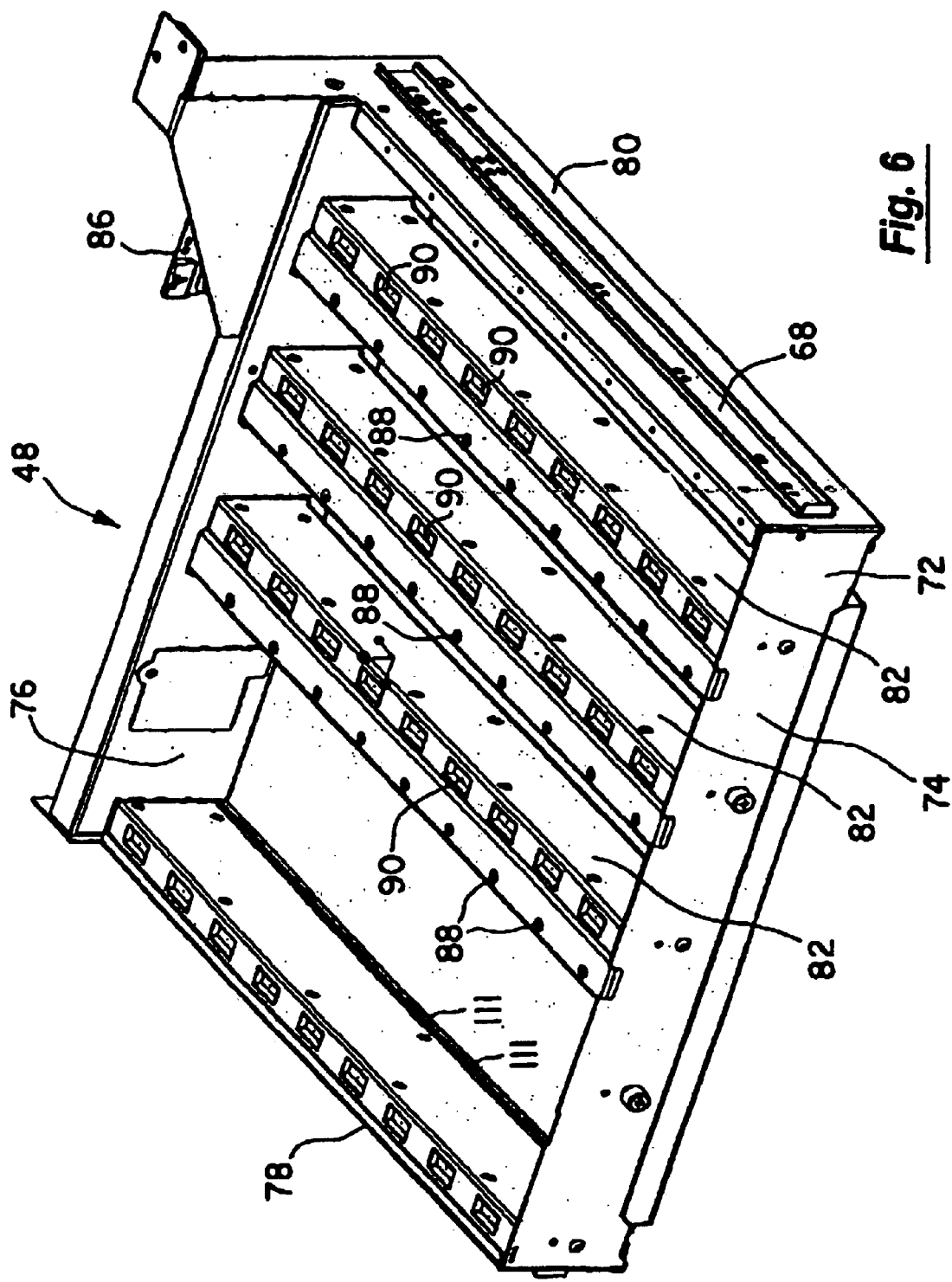

SECURED DISPENSING CABINET AND METHODS

BACKGROUND OF THE INVENTION

This invention relates generally to the field of dispensing and restocking items, and in particular to the dispensing and restocking of secured items, such as, but not limited to, pharmaceuticals. More specifically, the invention relates to dispensing devices and methods for dispensing a wide range of items upon request.

Many industries require items to be available for use at specific locations. For example, in the medical industry, practitioners find it convenient to place medical supply items or pharmaceuticals near where patients are being treated. Depending on the type of items to be dispensed, the environment where the items are to be used, and the like, a variety of dispensing cabinets have been proposed. Such cabinets may be provided in a variety of sizes, configuration and security levels and may conveniently be located near where the items are to be used. Examples of several successful dispensing cabinets are described in U.S. Pat. Nos. 6,272,394; 6,385,505; 5,805,455; 5,805,456; 5,745,366; 5,905,653; 5,927,540; 6,039,467; 6,151,536; 5,377,864; and 5,190,185, the complete disclosures of which are herein incorporated by reference.

Periodically, dispensing cabinets need to be restocked with items. Depending on the types of items to be restocked, the number of item types to be restocked, the level of security associated with the items, and the like, the restocking process can be challenging. Further, in some cases, nurse users may wish to have a different configuration for the dispensing cabinet. This may further complicate the restocking process as the configuration of the dispensing cabinet changes over time. Hence, this invention relates to dispensing devices and methods that facilitate restocking of items and reconfiguring of the dispensing devices, among other features.

BRIEF SUMMARY OF THE INVENTION

The invention provides various devices and methods for dispensing and restocking items. In some embodiments, such a dispensing device comprises a cabinet having a front, a back and a pair of sides that enclose an interior storage area. A dispenser frame is coupled to the cabinet and, in some cases, may be configured to be pulled out from the interior. The dispenser frame includes one or more dividers to which may be coupled one or more dispensing mechanisms that hold items to be dispensed. A lockable door may be coupled to the front of the cabinet so as to be positioned in front of the dispenser frame. Hence, by opening the door access to the dispenser frame is gained. Further, a dispense drawer may also be coupled to the cabinet below the storage dispenser frame. In this way, items dispensed from the dispensing mechanisms may fall into the dispense drawer.

One feature of the dispensing cabinet is that the dividers may be reconfigurable so that different types and/or arrangements of dispensing mechanisms may be provided in the same dispenser frame. Further, the dispense drawer may have approximately the same width as the dispenser frame. For example, the dispenser frame and dispense drawer may extend across the front of the cabinet. In this way, a single dispenser frame holding essentially all of the cabinet's dispensing mechanisms may be accessed by simply pulling out the dispenser frame. However, it will be appreciated that multiple dispense drawers could also be provided.

The dispensing cabinet may also have a computer system that is employed to store information, such as patient information, nurse user information, restock user or pharmacist information, item information, and the like. The computer system may also be used to facilitate operation of the dispensing cabinet, such as by controlling dispensing operations, restocking operations, and the like. The computer system may include various controllers, circuit boards, other circuitry or the like to determine the divider configuration, as well as to determine the addresses of the dispensing mechanisms and to control their operation. For example, in one aspect, the computer system may include a circuit board that is mounted to the dispenser frame and a controller that is mounted to the cabinet frame.

The computer system may also be used to sense the configuration of the dividers. For example, in one aspect, the computer system may be used to poll as to whether a divider is present at a particular location on the dispenser frame. This information may then be stored in the computer's memory.

The location or address of each dispensing mechanism on a particular divider may also be sensed and sent to the computer so that items for each dispensing unit may be assigned and stored in the computer. Conveniently, the dividers may include interfaces for interfacing with the dispensing mechanisms. When ready to assign an item to a dispensing mechanism, a sensing mechanism, such as a button or a switch, on the dispensing unit may be actuated to create a detectable event, such as a short in a circuit. In this way, the location of the divider may be determined and transmitted to the computer. Information on the item may then be input into the computer so that the computer will have a record of the address for each dispensing mechanism and its associated item.

To restock items into the dispensing cabinet, restock user identification information may be input into the computer along with a request to restock items. If approved, a restock list may be generated by the computer and selected by the restock user or pharmacist. This list may be transmitted from a host over a computer network. Optionally, a light on the door may light and a button on the door may be pushed to open the door, although in some cases the door may automatically open so that pressing of a button is not needed. The dispenser frame may then be pulled from the cabinet to gain access to the dispensing mechanisms. However, in some cases, the dispensing mechanisms may be accessed without needing to pull out the dispenser frame from the cabinet.

In one aspect, visual indicators, such as lights on the dispensing mechanisms that need restocking, may flash. The restock technician may then actuate the sensing mechanism on one of the dispensing mechanisms having a flashing light to tell the computer that that particular dispensing mechanism is to be restocked. The light may then continuously light and the name of the item to be restocked may be displayed by the computer. Optionally, the count of any existing items may be verified. Verification may also be performed to check expiration dates. Items may be restocked into the dispensing mechanism, their number entered, and the sensing mechanism actuated to indicate that restocking for that dispensing mechanism is completed. The light may then be turned off and the process repeated for another dispensing mechanism.

BRIEF DESCRIPTION OF THE DRAWINGS

FIG. 1A is a detailed view of a portion of a shelf of the cabinet of FIG. 1.

FIG. 5 is a more detailed view of the dispenser frame and dispensing mechanisms of FIG. 4.

FIG. 6 illustrates the dispenser frame of FIG. 4 with the dispensing mechanisms removed.

DETAILED DESCRIPTION OF THE INVENTION

Figure 1:
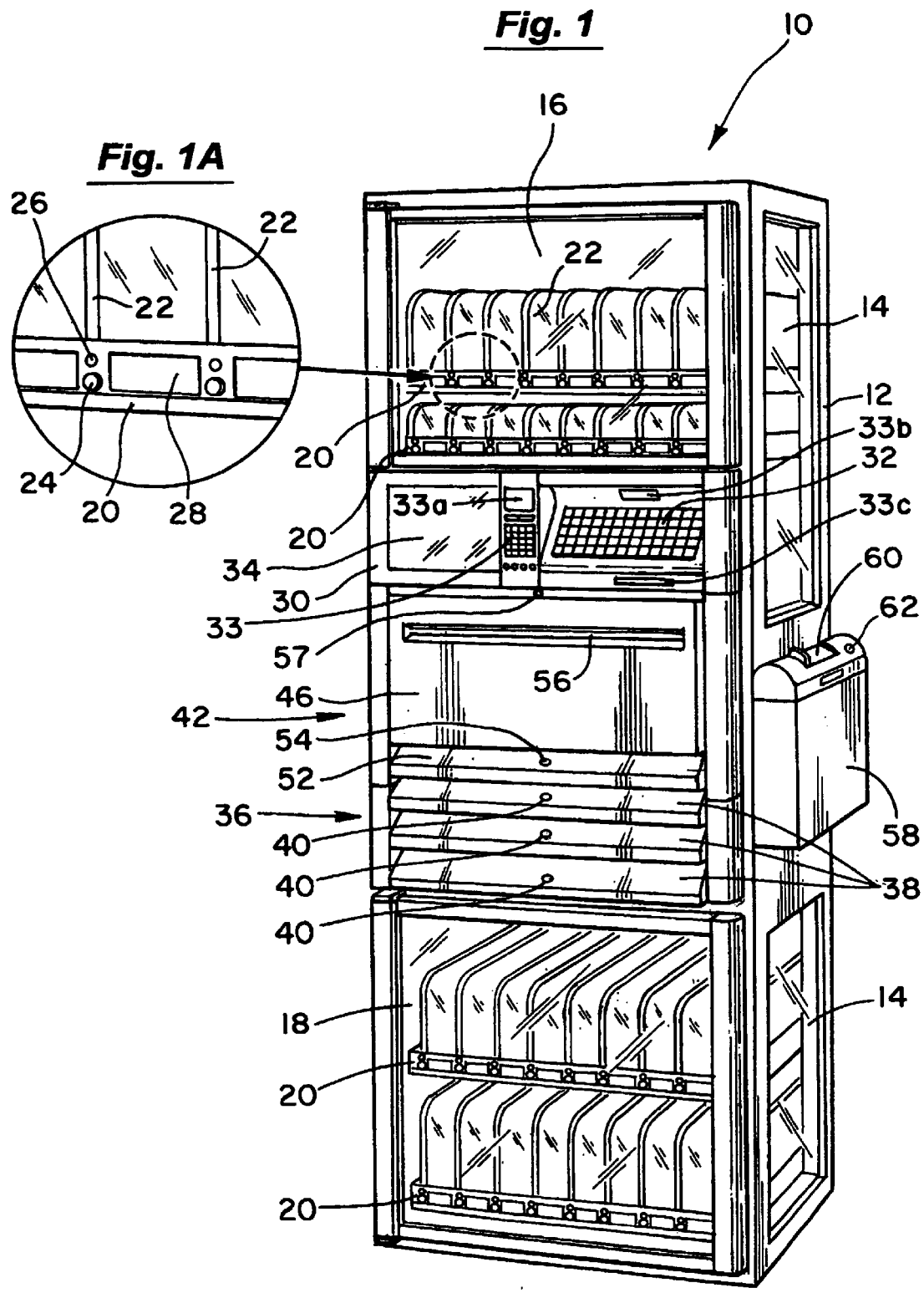
FIG. 1 is a front perspective view of a dispensing cabinet according to the invention.

The invention provides exemplary dispensing devices that may easily be reconfigured as well as restocked, among other features. The dispensing devices may have a dispensing unit that is secured within a cabinet, with access being provided to only authorized individuals. The dispensing unit may hold a variety of dispensing mechanisms that each hold items to be dispensed. Such an arrangement is particularly well suited for items that need to be secured, such as medications, drugs, and the like. If a nurse user is authorized, such items may be dispensed from the dispensing unit where they may fall into a dispense drawer that may be pulled from the cabinet to access the items.

The dispensing unit may include a dispenser frame that holds the dispensing mechanisms. The dispenser frame may also be pulled out from the cabinet to provide access to the dispensing mechanisms. Further, the dispenser frame may include reconfigurable dividers that hold the dispensing mechanisms. In this way, a wide variety of dispensing mechanism arrangements may be provided by reconfiguring the dividers and/or the location of the dispensing mechanisms on the dividers. Further, various types of dispensing mechanisms may be accommodated.

To reconfigure the unit, the dispenser frame may be withdrawn and the dividers may be reconfigured. Also, the dispensing mechanisms may be plugged into different locations on the dividers. Various sensing or detecting systems may be used to determine the configuration of the dividers and the addresses of the dispensing mechanisms on the dividers so that the computer system may associate items with each of the dispensing mechanisms. For example, when reconfiguring the location of a dispensing mechanism, a sensing mechanism, such as a button, may be pressed on the dispensing mechanism to indicate the new location of the dispensing mechanism. This is in stark contrast to prior art systems where physical address labels have been placed onto each divider. If the configuration of such systems changed, these labels needed to be changed as well.

Such an arrangement also facilitates initial stocking and restocking. To initially stock a dispensing mechanism, a sensing mechanism, such as a button on the dispensing mechanism, may be pushed to identify the dispensing mechanism. The type and quantity of the item to be stocked may then be entered into the computer. By pressing the button, the computer may detect the dispensing mechanism being accessed and may assigned the item to that address.

To restock, a restock list may be selected. The dispensing cabinet's computer may be coupled to a network to permit various restock information to be downloaded to the computer. This information may be stored at the computer, or else accessed when needed over the network. Visual indicators, such as lights, LEDs, or the like, on the dispensing mechanisms that are to be restocked may then be actuated to guide the restock user or pharmacist through the restocking process. The button on the dispensing mechanism may be pushed to identify the dispensing mechanism that is being restocked, and the expected quantity may be displayed on the display screen. A count may be verified, the dispensing mechanism restocked, and the quantity entered.

Referring now to FIG. 1, one embodiment of a dispensing cabinet 10 will be described. Cabinet 10 may conveniently be constructed from a cabinet frame 12 with various transparent panels 14. Cabinet 10 further includes a pair of doors 16 and 18 that enclose a series of shelves 20 within cabinet 10. As also shown in FIG. 1A, shelves 20 may conveniently be divided into various storage locations using adjustable dividers 22. Further, associated with each storage location may be an item button 24 that may be pressed to record the removal of items from or placement of items into each storage location. A light 26 may also be positioned adjacent each item button to guide the restock user to a specific storage location. Further, a label 28 may be associated with each storage location include information on the items stored in a particular storage location. Optionally, doors 16 and 18 may be locked and only opened when appropriate identification information has been entered into a computer 30. Hence, to remove an item from one of the shelves 20, a nurse user may enter appropriate identification information into computer 30.

To facilitate the entry of information, computer 30 includes a traditional keyboard 32 and a key pad 33 containing numeric keys. A touch pad 33a may be disposed above key pad 33 and used to control a pointer on a display screen 34. Disposed below key pad 33 are keys to control the contrast of display screen 34 and to control the sound that may be emitted from a speaker 33b. Disposed below keyboard 32 is a receipt port 33c through which printed receipts may pass. Conveniently, the panel containing keyboard 32 may be rotated downward to gain access to the receipt printer.

One use of the various input devices on computer 30 is to permit the nurse user to select one or more items that are to be removed. Conveniently, a list of items and the entered information may conveniently be displayed on the display screen 34. Further, display screen 34 may be a touch screen display that permits various items to be selected simply by touching them on display screen 34. Computer 30 may be coupled to any type of computer network to permit various information to be supplied to computer 30. For example, restock lists may be transmitted from a central server or host computer system.

When the appropriate items have been selected, doors 16 and 18 may be unlocked (in cases where doors 16 and 18 are already locked) and the appropriate lights 26 may be lighted to guide the nurse user to the items selected. Upon removal of the items, the nurse user may press item buttons 24 a number of times corresponding to the number of items removed. A similar process may be used for restocking items into the storage locations. A further discussion of such a process is described in U.S. Pat. Nos. 6,272,394; 6,385,505; 5,805,455; 5,805,456; 5,745,366; 5,905,653; 5,927,540; 6,039,467; 6,151,536, previously incorporated herein by reference and will not be described further.

Cabinet 10 further includes a pharmacy section 36 with various drawers 38 for holding pharmaceutical items or other types of items that need additional security. When appropriate information has been entered into computer 30, the appropriate drawers 38 may be unlocked and lights 40 on the drawers lighted to guide the nurse user to the appropriate doors. Drawers 38 may conveniently include various bins which may optionally have lockable lids to provide additional security to the items. The lids corresponding to bins that have the selected items may be unlocked and nurse users may be guided to the unlocked bins using lights in a manner similar to that described with shelves 20. Examples of various types of drawer and bin arrangements that may be used in pharmacy section 36 may be found in at least some of U.S. Pat. Nos. 6,272,394; 6,385,505; 5,805,455; 5,805, 456; 5,745,366; 5,905,653; 5,927,540; 6,039,467; 6,151, 536, previously incorporated herein by reference, and will not be described further.

Figure 2:
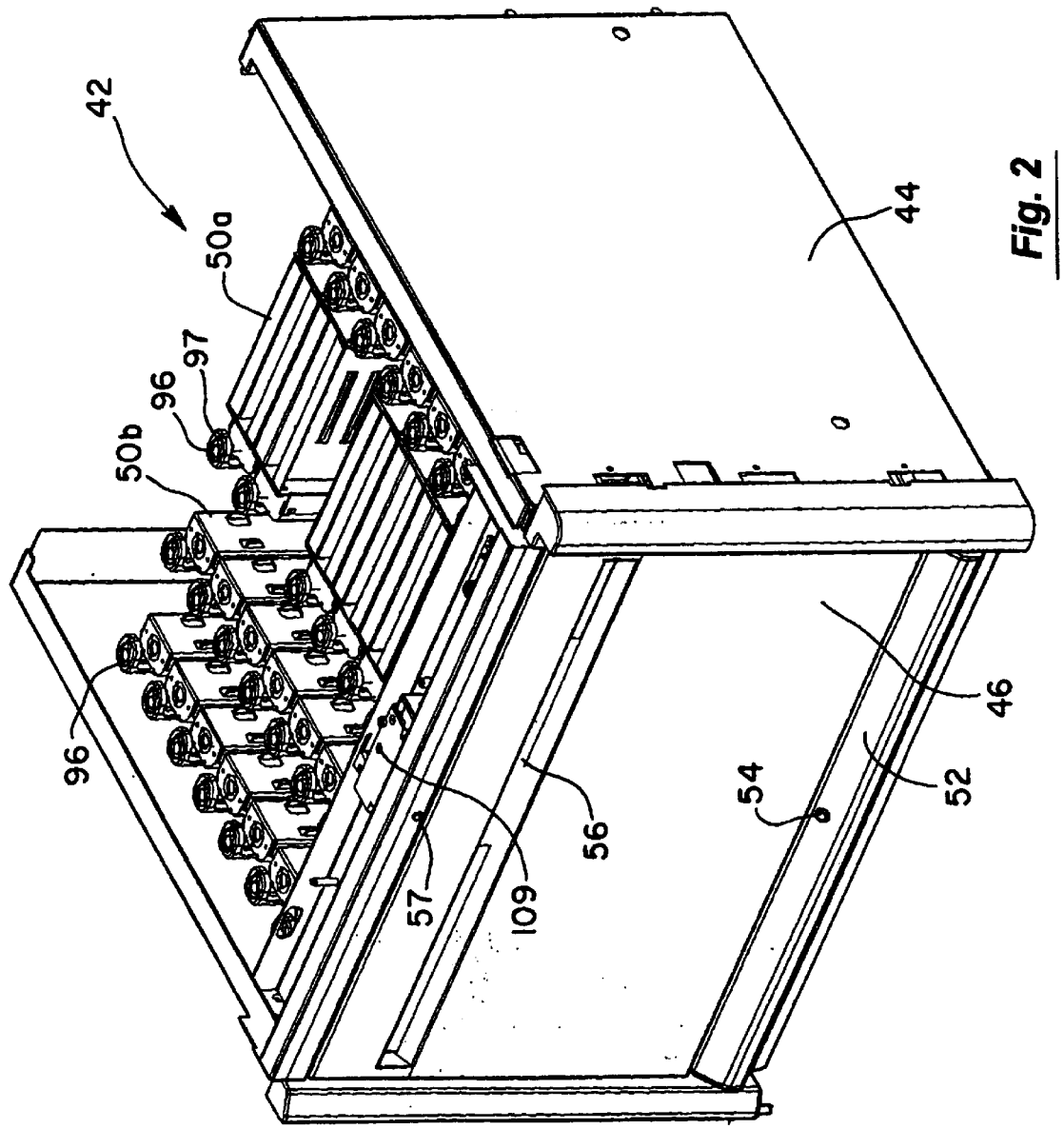
FIG. 2 illustrates a pharmaceutical dispensing unit f the cabinet of FIG. 1

Pharmacy section 36 further includes a dispensing unit 42 that is also illustrated in greater detail with reference to FIGS. 2–5. Briefly, dispensing unit 42 comprises a dispensing unit frame 44 that is insertable into cabinet frame 12 of cabinet 10. Coupled to dispensing unit frame 44 is a door 46 that may be opened to provide access to a dispenser frame 48 (see FIG. 3). As described in greater detail hereinafter, dispenser frame 48 may be withdrawn from dispensing unit frame 44 to provide access to various dispensing mechanisms 50 (see for example FIGS. 4 and 5). As best shown in FIG. 2, disposed below dispenser frame 48 is a dispense drawer 52 that receives items that fall from dispensing mechanisms 50 after such items have been selected at computer 30 (see FIG. 1). Conveniently, dispense drawer 52 may include a light 54 to guide the nurse user to the dispense drawer during dispensing operations. Conveniently, a handle 56 (see FIGS. 1 and 2) may be provided on door 46 to facilitate opening of door 46.

In some cases, dispensed items may need to be returned to cabinet 10. In some situations, various laws and regulations prohibit dispensed items from being placed back into cabinet 10. As such, attached to cabinet 10 may be a return unit 58 having a slidable (or rotatable) door 60 that may be opened to permit the item to be placed into unit 58. When returning the item, information regarding the return may be entered into computer 30. Conveniently, a light 62 on return unit 58 may be lighted to indicate to the nurse user that the item may be returned. Return unit 58 is preferably configured so that once an item is placed into the unit, the item cannot be returned from unit 58 unless a restock user or technician is authorized to gain access to return unit 58. For example, a restock technician may be required to enter appropriate information into computer 30 to cause return unit 58 to unlock to allow access to the items within return unit 58.

Although one specific arrangement of cabinet 10 has been described, it will be appreciated that dispensing unit 42 may be used with a variety of dispensing cabinets. For example, dispensing unit 42 may be placed within a cabinet that is used solely for dispensing pharmaceuticals and may only include drawers similar to drawers 38. As another alternative, dispensing unit 42 may be placed in a cabinet that only includes shelves that are similar to shelves 20. Further, dispensing unit 42 may be used in cabinets having multiple shelves and/or drawers that are placed side by side in a vertical arrangement. Also, the dispensing cabinet may include multiple dispensing units 42. These may be sized to the same size, or may be a different size. Still further, in some cases such dispensing cabinets may include other types of shelves, racks, drawers, and the like to facilitate the storage of items. Various examples of shelf, rack, and drawer designs are described in U.S. Pat. Nos. 6,272,394; 6,385, 505; 5,805,455; 5,805,456; 5,745,366; 5,905,653; 5,927, 540; 6,039,467; 6,151,536; 5,377,864; and 5,190,185, previously incorporated herein by reference.

Figure 3:
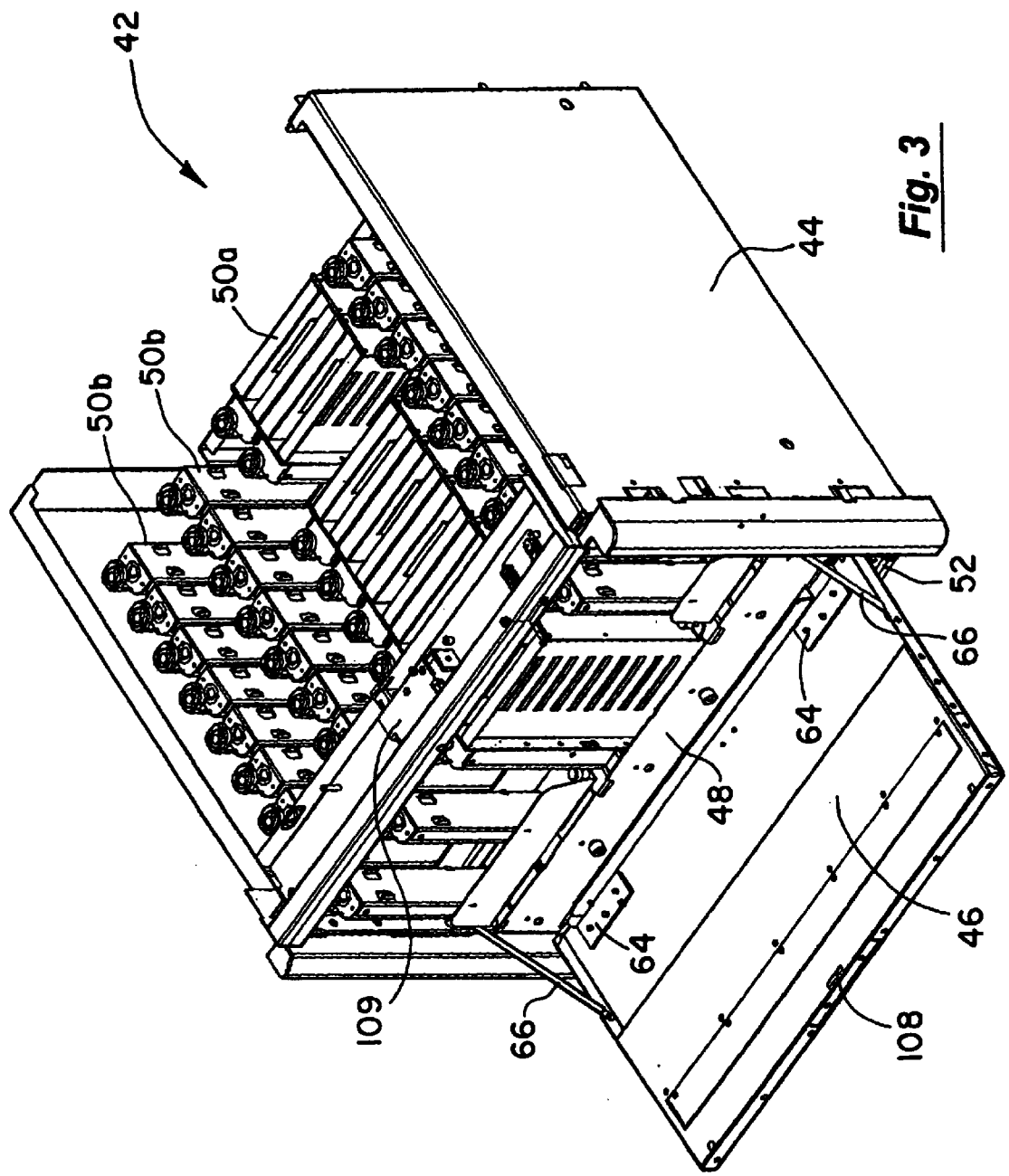
FIG. 3 illustrates the unit of FIG. 2 having dispensing mechanisms and showing a front door opened.
Figure 4:
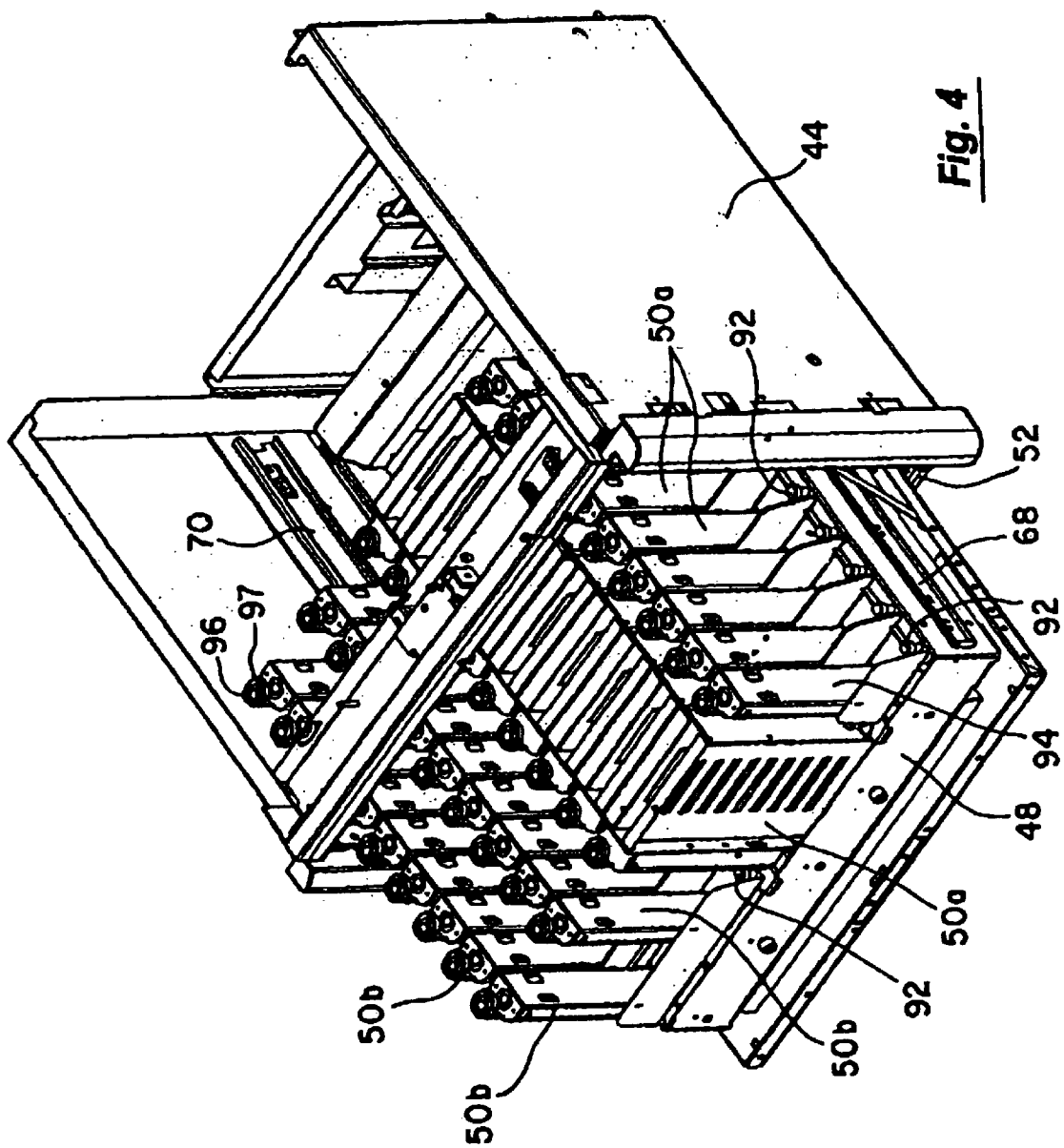
FIG. 4 illustrates the unit of FIG. 3 with a dispenser frame having the dispensing mechanisms withdrawn.

Referring now to FIGS. 2–6, construction and operation of dispensing unit 42 will be described in greater detail. As best shown in FIG. 3, door 46 is coupled to frame 44 using hinges 64. These permit door 46 to be opened to gain access to dispenser frame 48. Conveniently, arms 66 may be used to limit the extent to which door 46 may be opened so that it does not interfere with the opening of dispense drawer 52 as best illustrated in FIG. 4. Conveniently, dispenser frame 48 and frame 44 may include a track system 68 and 70 (and dispense drawer 52 and frame 44 may also include a similar track system) to permit dispense drawer 52 and dispenser frame 48 to easily be withdrawn from frame 44 as shown in FIG. 4.

As best shown in FIG. 6, dispenser frame 48 is constructed of a rectangular frame 72 having a front 74, a back 76 and two sides 78 and 80. Frame 72 is generally open except for a set of adjustable dividers 82 that are positioned between front 74 and back 76. Optionally, another divider may be coupled to side 78 as illustrated in FIG. 6.

Front 74 and back 76 may include a set of mechanical interfaces, such as slots, holes, grooves, cut outs or the like to interface with tabs, protrusions, or the like on dividers 82. In this way, a blind matable connection between the dividers 82 and frame 72 may easily occur. Further, screws 84 may be used to securely couple dividers 82 to frame 72 once in place. By providing a series of mechanical interfaces, the placement of dividers 82 in dispenser frame 48 may be varied along front 74 and back 76. Further, any number of dividers 82 may be coupled to dispenser frame 48. In this way, the wide variety of dispensing mechanisms that are to be coupled to dividers 82 may be accommodated. Back 76 may also include a series of electrical interfaces that interface with electrical interfaces on dividers 82 when they are mechanically coupled to dispenser frame 48. Dispenser frame 48 may also include a circuit board 86 (see FIG. 6) that may be used to facilitate communications between circuitry associated with the dividers 82 and computer 30. One capability of the circuitry used with cabinet 10 is the ability to detect the specific configuration of dividers 82 within dispenser frame 48. For example, appropriate circuitry in combination with computer 30 may be used to poll each one of the interfaces to determine if one of the dividers 82 is connected to that interface. This may be detected, for example, by sensing a short or low voltage signal that is created when divider 82 is coupled to a specific electrical interface.

Hence, dispensing unit 42 may include a single dispenser frame 48 that has essentially the same width as dispense drawer 52 that is positioned beneath dispenser frame 48. Further, dispense drawer 52 may have essentially the same width as other drawers and/or shelves in the dispensing cabinet. In this way, a single dispenser frame may be employed to hold a wide variety of dispensing mechanisms that may all be simultaneously accessed by withdrawing dispenser frame 48. Further, the configuration of dispenser frame 48 may easily be varied simply by changing the configuration and/or number of dividers 82 that are included within dispenser frame 48. Further, the configuration of dividers 82 may be automatically sensed so that the dispensing cabinet will know the configuration of the dividers that will subsequently be needed for dispensing and/or restocking operations as described in greater detail hereinafter.

Each divider 82 includes mechanical interfaces 88 and electrical interfaces 90 which are employed to receive dispensing mechanisms 50. As will be appreciated, a wide variety of dispensing mechanisms may be used. For convenience of discussion, the dispensing mechanisms in general will be referred to with reference numeral 50. Specific types of dispensing mechanisms will use the same reference numeral followed by an "a", "b", etc. For example, dispensing mechanisms 50*a* are syringe type dispensers, and dispensing mechanisms 50*b* are cassette type dispensers. Conveniently, two dispensing mechanisms 50*b* may be coupled together to form a double cassette dispenser. Mechanical interfaces 88 may conveniently comprise a threaded opening for receiving a screw. Also, it will be appreciated that other connectors may be used, such as quick release mechanisms, detents, snap fits, other tool-less connections, and the like. As best shown in FIG. 4, dispensing mechanisms 50*b* are screwed to one of the dividers 82 using a screw 92. Dispensing mechanism 50*b* then extends to an adjacent divider 82 to permit an electrical interface 94 on dispensing mechanism 50*b* to interface with electrical interface 90 of divider 82. In this way, dispensing mechanisms 50*b* may be coupled to dispenser frame 48 in a "plug and play" manner simply by plugging the dispensing mechanism into the appropriate electrical interface 90 and then using screw 92 to screw the dispensing mechanism to mechanical interface 88. The other dispensing mechanisms may be connected to dividers 82 in a similar manner.

As previously described, dividers 82 may be placed in any configuration to accommodate the number and/or size and/or type of dispensing mechanism 50 that may be used. For example, although illustrated with several specific types of dispensing mechanisms, it will be appreciated that a wide variety of other dispensing mechanisms may be used that are capable of dispensing items based on an electrical signal that is passed through electrical interface 90 via control circuit board 86. Some examples of such dispensing mechanisms that may be used are described in U.S. Pat. Nos. 5,377,864; and 5,190,185, previously incorporated herein by reference. Hence, it will be appreciated that the invention is not intended to be limited to a specific type of dispensing mechanism.

In order to control dispensing and restock operations, computer 30 (see FIG. 1) needs to know the address of each dispensing mechanism and the type of item stored in that dispensing mechanism. This may easily be accomplished since the location of each divider 82 on dispenser frame 48 is automatically determined. In a similar manner, the address for each dispensing mechanism 50 may be determined by using a similar polling process since each dispensing mechanism is electrically coupled to one of the dividers 82. Conveniently, each dispensing mechanism 50 may include a button 96 that may be pressed by the restock user to produce a detectable event, such as a short or a low-voltage signal that may be detected by a circuit board that is disposed within each divider. The circuit boards are disposed below the connectors and contain address information for each of the dispensing mechanisms. The circuit boards may also be used to control actuation of the dispensing mechanisms and any sensing mechanisms. The address information may be transmitted from the circuit boards to computer 30. In this way, computer 30 may know the address of a particular dispensing mechanism when button 96 is pressed. At the same time, the restock user may assign a given item to that particular dispensing mechanism and enter this into computer 30 so that computer 30 will have a record of the address of each dispensing mechanism and its associated item. Conveniently, dispensing mechanisms 50 may also include lights 97 that may be used to guide a restock technician to a particular dispensing mechanism during restocking operations as described in greater detail hereinafter. In some cases, the light may be provided on the divider, and the dispensing mechanisms 50 may have a light pipe, such as a plastic conduit, to display the light. In some cases, the dispensing mechanisms may include an identifier that uniquely identifies each dispensing mechanism. This information may be detected by the circuit board and sent to computer 30 so that computer 30 may assign a specific dispensing mechanism to a specific location. If the particular dispensing mechanism is removed to another location, computer 30 may detect the displacement and produce a warning signal. Examples of identifiers that may be used include RFID tags, EPROM chips, bar codes and the like. If such identifiers are used, configuration of the dispensing unit may occur automatically since computer 30 will know each specific dispensing mechanism and its location upon connection of the dispensing mechanism.

Referring now to FIGS. 3–5, construction of dispensing mechanisms 50*a* will be described. However, as previously set forth, dispenser frame 48 may utilize a wide variety of dispensing mechanisms and the invention is not intended to be limited to a specific type of dispensing mechanism. Dispensing mechanisms 50*a* each comprise a housing 98 having an opening 100 that is configured to receive items in a stacked manner. For example, opening 100 may conveniently be used to store syringes. Disposed at the bottom of dispensing mechanism 50*a* is a dispensing arrangement that is operated by a solenoid to dispense a single item each time the solenoid is operated. Alternatively, dispensing may occur by actuating a motor, other mechanical actuator or the like. Hence, after receiving signals from the computer 30, the circuit board within the appropriate divider may be used to send a signal to the appropriate solenoid, motor or other mechanism to cause a dispensing arrangement to operate and dispense a single item. The dispensed item then falls into dispense drawer 52 that may be pulled from cabinet 10 to access the dispensed item. A more detailed described of how such a dispensing arrangement may operate is set forth in U.S. Pat. Nos. 5,377,864; and 5,190,185, previously incorporated herein by reference.

Figure 5A:
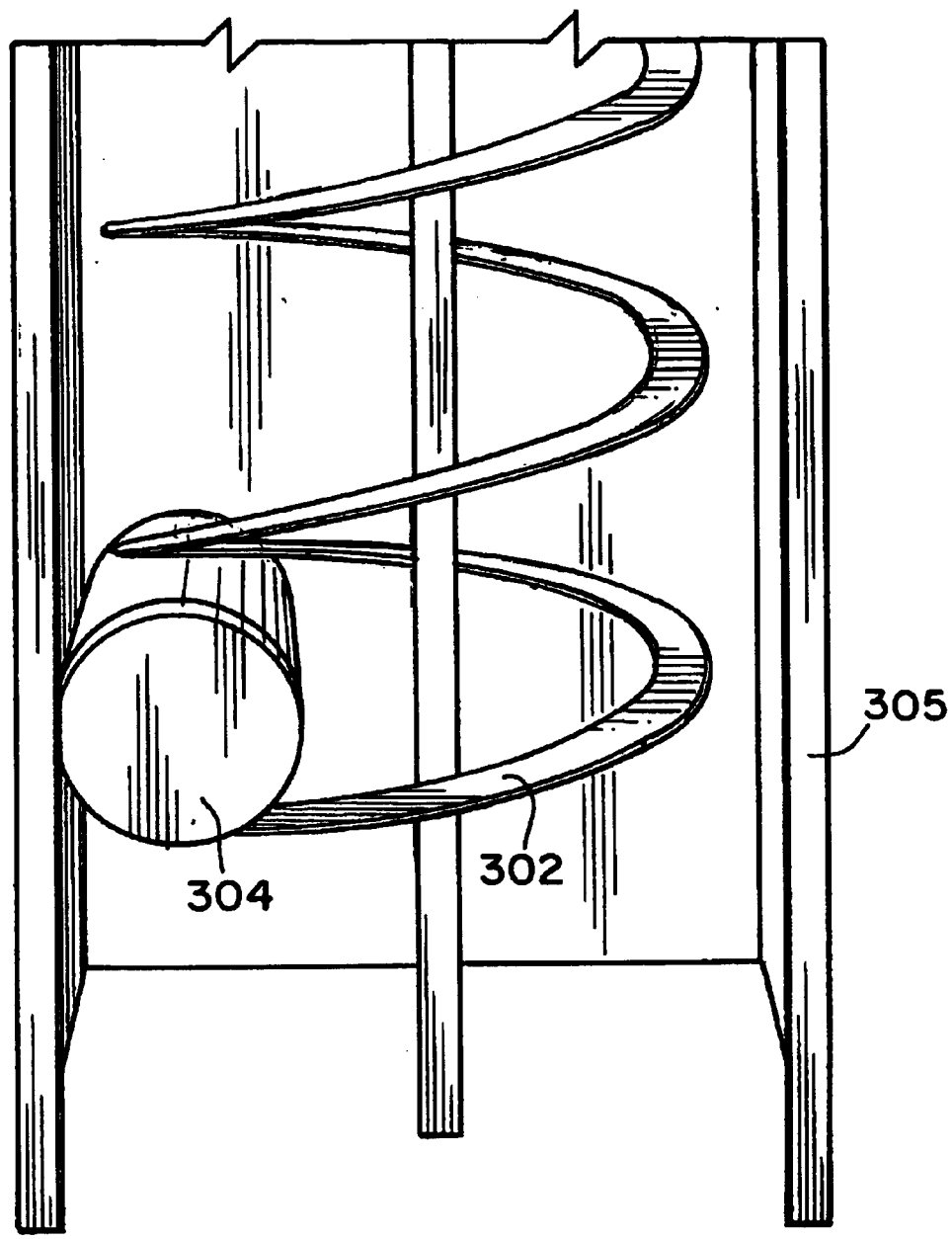
FIG. 5A illustrates a dispensing coil of one particular dispensing mechanism.
Figure 5B:
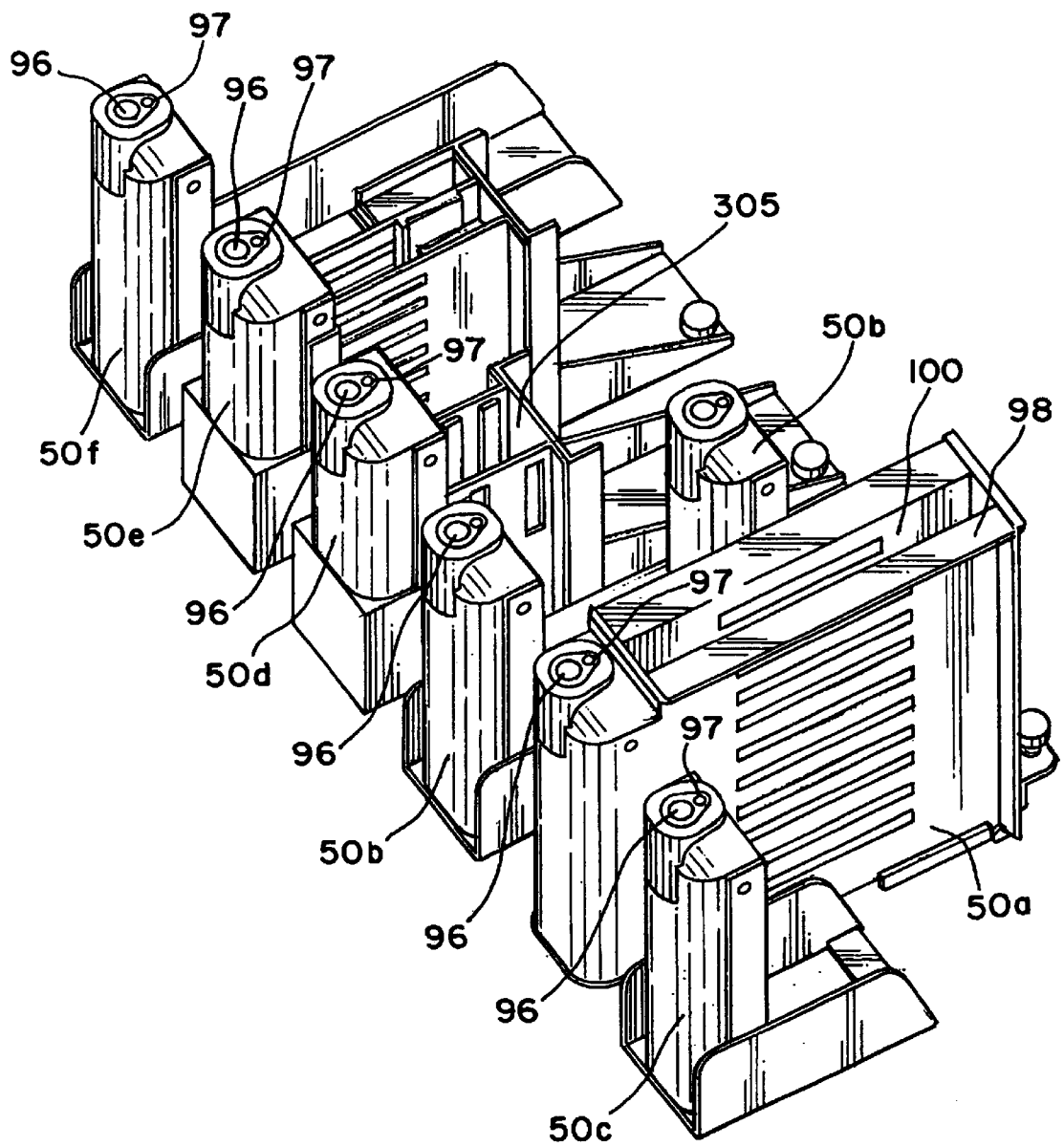
FIG. 5B illustrates a set of dispensing mechanisms according to the invention.

It will be appreciated that other dispensing mechanisms may be used to hold other types of items such as vials, ampoules, cassettes, pills, tablets, other oral solids, and the like. For example, dispensing mechanisms 50*b* may be utilized to dispense pill packages, small ampoules, vials, and the like. Dispensing mechanisms 50*b* include a motor having a vertically oriented output shaft. Coupled to the output shaft is a gear system that is used to rotate a helical coil 302 surrounding a shaft that is contained within a housing 305. As best shown in FIG. 5A, a vial 304 is held in coil 302 and is moved downward when coil 302 is rotated. When vial 304 reaches the bottom of coil 302 is it dispensed and falls into dispense drawer 52. Hence, items may be dispensed from dispensing mechanisms 50b simply by sending an appropriate signal from computer 30 to the motor that rotates coil 302.

When utilizing other types of dispensing mechanisms, circuit board 86 may be configured to send other signals to actuate other types of equipment. For example, other types of dispensing mechanisms that may be used are described in FIG. 5B. These may conveniently be coupled to dividers 82 in a manner similar to that previously described. One of these dispensing mechanisms is a small cassette type dispenser 50c that is similar to dispensing mechanism 50b except for its size. Dispensing mechanism 50c is particularly useful in dispensing pill packages. Another dispensing mechanism is a 5 ml vial dispensing mechanism 50d that is solenoid actuated in a manner similar to dispensing mechanism 50a. Also shown is a 5 ml ampoule dispensing mechanism 50e that dispenses 5 ml ampoules using a solenoid in a manner similar to dispensing mechanism 50a. A large cassette dispensing mechanism 50f is employed to dispense pill packages, small ampoules, and vials. Dispensing mechanism 50f may be motor actuated in a manner similar to dispensing mechanism 50b.

Figure 5C:
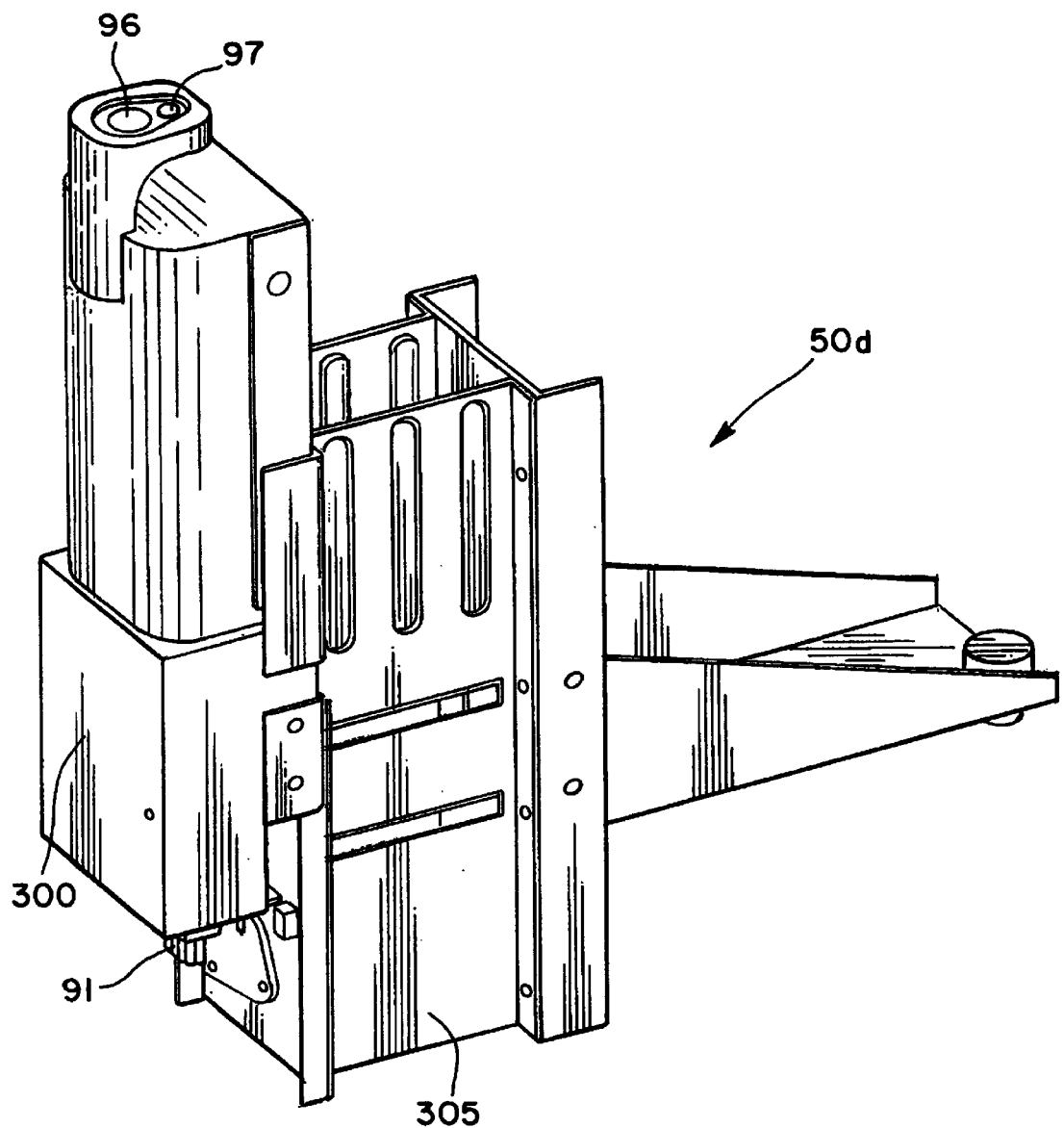
FIG. 5C is a more detailed view of a cassette type dispensing mechanism according to the invention.

Dispensing mechanism 50d is illustrated in greater detail in FIG. 5C and is constructed of a housing 300 that houses a solenoid. The solenoid is used to operate a trap door system similar to that described in connection with dispensing mechanism 50a to dispense its contents. As also shown in FIG. 5C, dispensing mechanism 50d includes an electrical connector 91 that is configured to be inserted into connector 90 when dispensing mechanism 50d is coupled to a divider.

Hence, by utilizing a reconfigurable divider system, and by configuring the divider so that a wide variety of dispensing mechanisms may be interfaced in a plug and play manner, dispenser frame 48 may be easily configured to accommodate a wide variety of dispensing mechanism types as well as arrangements. The divider configurations may automatically be determined and addresses for each of the dispensing mechanisms may easily be assigned since the appropriate circuitry may easily detect the location of each dispensing mechanism and may supply this information to computer 30 where items may be assigned to specific dispensing mechanisms. Although not intended to be limiting, Tables 1–5 below illustrate various types of arrangements that are possible with dispenser frame 48.

TABLE 1

| Cassette Dispenser | Cassette Dispenser | Cassette Dispenser | Cassette Dispenser | Cassette Dispenser |
|---|---|---|---|---|
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |

Table 1 describes an arrangement where dispenser frame 48 is configured to hold a maximum of five cassette-type dispensing mechanisms across the dispenser frame.

TABLE 2

| Syringe Dispenser | Cassette Dispenser | Syringe Dispenser |
|---|---|---|
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |

Table 2 shows an arrangement where a dispenser frame may hold a maximum of two syringe-type dispensing mechanisms and one cassette-type dispensing mechanism across the dispenser frame.

TABLE 3

| Syringe Dispenser | Cassette Dispenser | Cassette Dispenser | Cassette Dispenser |
|---|---|---|---|
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |
| Syringe Dispenser | Cassette Dispenser | Cassette Dispenser | Cassette Dispenser |

Table 3 illustrates an arrangement for holding a maximum of one syringe-type dispensing mechanism and three cassette-type dispensing mechanisms across the dispenser frame. The configuration between the syringe-type dispensing mechanisms and cassette-type dispensing mechanisms may be configured by removing and replacing dividers 82 as previously described.

TABLE 4

| Top View | | |
|---|---|---|
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Syringe Dispenser | Cassette Dispenser | Syringe Dispenser |
| Cassette Dispenser | Cassette Dispenser | Cassette Dispenser | Syringe Dispenser |
| Cassette Dispenser | Cassette Dispenser | Cassette Dispenser | Syringe Dispenser |
| Cassette Dispenser | Cassette Dispenser | Cassette Dispenser | Syringe Dispenser |

TABLE 4-continued

| Top View | | | |
|---|---|---|---|
| Cassette Dispenser | Cassette Dispenser | Cassette Dispenser | Syringe Dispenser |

Table 4 illustrates a configuration having dividers that define two double wide spaces and one single wide space. The double wide spaces may be used to hold syringe-type dispensers while the single wide spaces may hold cassette-type dispensers. Further, one of the double wide spaces may also be used to hold two cassette-type dispensing mechanisms as well.

TABLE 5

| Top View | | | | |
|---|---|---|---|---|
| Syringe Dispenser | | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |
| Cassette Dispenser | Cassette Dispenser | Cassette Dispenser | Cassette Dispenser | Cassette Dispenser |

Table 5 illustrates a dispenser frame configuration having dividers that define one double wide space and three single wide spaces. Further, the double wide space may be configured to hold two cassette-type dispensers in addition to syringe-type dispensers.

Another feature of dispensing unit 42 is that circuit board 86 is incorporated into dispenser frame 48. In this way, circuit board 86 may easily be accessed for maintenance, repair or replacement simply by withdrawing dispenser frame 48 from dispensing unit 42. Further, incorporating circuit board 86 into dispenser frame 48 permits the dividers to be electrically coupled to electrical connectors using a blind matable connection. Circuit board 86 may be a passive connector board that channels commands to other boards used in connection with the dispensing cabinet. These other controllers may be on the same internal communication bus and may be used to filter out communications on non-functioning boards to allow the system to continue operating with a troublesome component. Circuit board 86 may be electrically coupled to another controller (that may in turn be coupled to frame 44 and electrically connected to computer 30) using various ribbon cables or other communication devices. These cables may be routed along the sides of dispensing unit 42 so as to not interfere with travel of dispenser frame 48 as it is withdrawn and pushed back into dispensing unit 42. The control board on frame 44 may be used as the main controller for operating the components associated with dispensing unit 42. Its functions may include manipulating and distributing power to the components in dispensing unit 42, generating module communications and interacting with the communication bus of the dispensing cabinet, and the like. The communications generated may include, but are not limited to, reading hardware configuration, auto calibrating a dispensing sensor system and running diagnostic scripts.

Various security features may also be provided to dispensing unit 42. For example, as best shown in FIG. 3, door 46 may include an opening 108 for receiving a latch of a latching mechanism 109 that may be employed to lock door 46 to frame 44. In this way, access to dispenser frame 48 may be prevented until appropriate identification information is entered into computer 30. After such information has been entered, computer 30 may send a signal to operate latching mechanism 109 and permit door 46 to be unlocked.

Another feature is the use of a sensing system to detect when items have been dispensed from dispensing mechanisms 50 where they fall into dispense drawer 52. The sensing mechanism may transmit a beam or other signal below the dispensing mechanisms that may be interrupted as items fall into dispense drawer 52. One exemplary type of sensing system comprises IR detectors (hidden from view) and emitters 111 (see FIG. 6). The IR emitters 111 may be arranged along one of the dividers 82 to emit signals that are directed onto the opposite divider 82 that contains the detectors. In this way, the signal is sent laterally between the dividers. The sensing system may also have an automatic calibration feature for each IR emitter-detector. A calibration may be performed just prior to a dispensing event. Such a calibration may be beneficial in cases where light conditions change over time, such as during a bright day when ambient light enters when the frame is opened. By calibrating just prior to dispensing, the sensing system may be configured to sense the dispensing, even under different lighting conditions. As one alternative, each dispensing mechanism may be associated with it own sensor, including any of those described herein. In this way, each time a particular dispensing mechanism dispenses an item, the sensor may correlate the dispensing with the particular dispensing mechanism. Another way to accomplish such a feature is by using a second set of emitters and detectors that are mounted across the entire length of the dispenser frame (such as between front 74 and back 76 as shown in FIG. 6). In this way, two sets of emitters and detectors and positioned perpendicular to each other. In this way, the X and Y position of the item may be detected as it is dropped from a dispensing mechanism. This information may be sent to computer 30 to indicate the exact dispenser from which the item was dispensed.

Another example of such a sensing system may be a vertical cavity surface emitting laser (VCSEL) sensing system. Such a system comprises a laser that transmits a signal across the bottoms of dispensing mechanisms 50. The laser is configured to reflect off a micro prism reflector so that the signal may be reflected back to a location near the laser source. If this signal varies, it may be used to detect that an item has been dispensed. Such a sensing system may be a VCSEL laser sensing system, from Honeywell. In this way, a confirmation may be made that an item was in fact dispensed when requested by the nurse user at computer 30. Such a sensing system is advantageous in that it reduces calibration times and is able to sense across the entire dispenser frame to reduce or eliminate errors.

Figure 7:
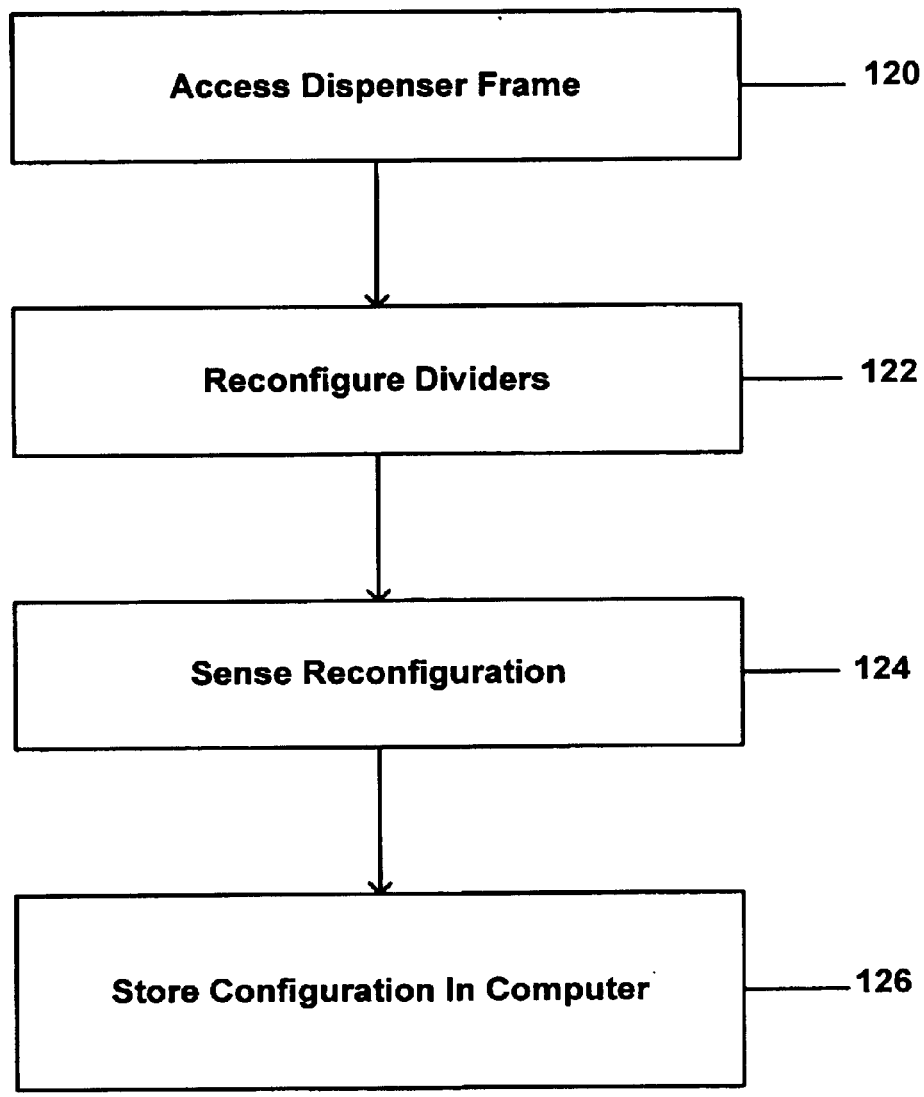
FIG. 7 is a flowchart illustrating one method for reconfiguring the dividers of a dispensing dispenser frame.

Referring now to FIG. 7, one method for configuring dividers 82 on dispenser frame 84 will be described. Conveniently, the process illustrated in FIG. 7 may be described in connection with the dispensing cabinet 10 and dispensing unit 42 as just described in connection with FIGS. 1–6. Initially, the restock user may log into the system using computer 30 and place computer 30 into the configuration mode. The restock user may then specify a zone that is to receive dispensing unit 42 so that its position within cabinet 10 is known. To configure the dividers, the dispenser frame is accessed as shown in step 120. This may conveniently be accomplished by withdrawing dispenser frame 48 from dispensing unit 42. The dividers may then be reconfigured in the desired position as illustrated in step 122. Control circuit board 86 may then be used to sense the reconfiguration of the dividers as illustrated in step 124. This information is transmitted to computer 30 for storage as shown in step 126. Optionally, computer 30 could be configured to allow the restock user to manually input the configuration of the dividers so that a sensing system would not be needed.

Figure 8:
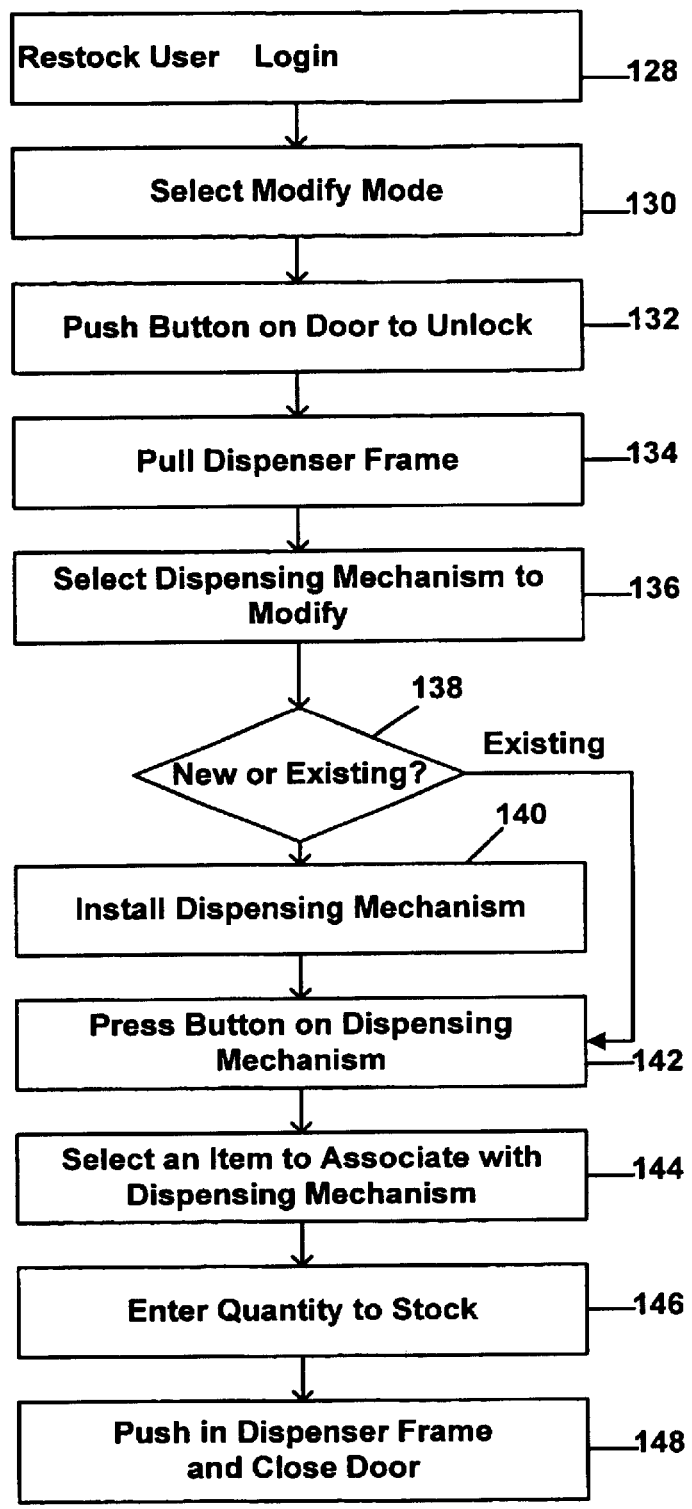
FIG. 8 is a flowchart illustrating one method for assigning items to dispensing mechanisms.

Referring now to FIG. 8, one method for configuring the dispensing mechanisms within dispenser frame 48 will be described. Initially, the restock user logs in as illustrated in step 128 by entering appropriate information into computer 30. The restock user may then select a modify mode at computer 30 as illustrated in step 130. Optionally, door 46 on dispensing unit 42 may include a button 57 that the restock user may push to unlock door 46 as illustrated in step 132. In so doing, latching mechanism 109 operates to unlatch the latch so that restock user may open the door. As shown in step 134, the restock user may then pull dispenser frame 48 out from the dispensing cabinet. As previously described, one feature of the invention is that a single dispenser frame may be employed so that the restock user may conveniently access all of the dividers when reconfiguring the dispensing mechanisms.

Once the dispenser frame is pulled out, the restock user may select a specific dispensing mechanism to modify as shown in step 136. The type of modification may depend on whether the dispensing mechanism is already coupled to a divider and simply needs to be reassigned a new type of item, or whether the dispensing mechanism is a new dispensing mechanism that is to be coupled to the divider. A query as to this effect is illustrated in step 138. If the dispensing mechanism is a new dispensing mechanism that is to be added to divider, the dispensing mechanism is installed to the divider as illustrated in step 140. As previously described, this may be accomplished by screwing a screw 92 into mechanical interface 88. As shown in step 142, button 96 may then be pressed to identify to computer 30 the specific dispensing mechanism that is being modified. This process is performed for both new and existing dispensing mechanisms. Display screen 34 may then permit the restock user to select an item to associate with the selected dispensing mechanism as illustrated in step 144. Since computer 30 knows the correct dispensing mechanism on a given divider once button 96 is pressed, it may assign that dispensing mechanism the selected item. As shown in step 146, the restock user may also enter the item quantity into the dispensing mechanism. Steps 136–146 may then be repeated to modify other dispensing units. When the process is finished the dispenser frame may be pushed back into the dispensing cabinet and the door closed as illustrated in step 148.

Figure 9:
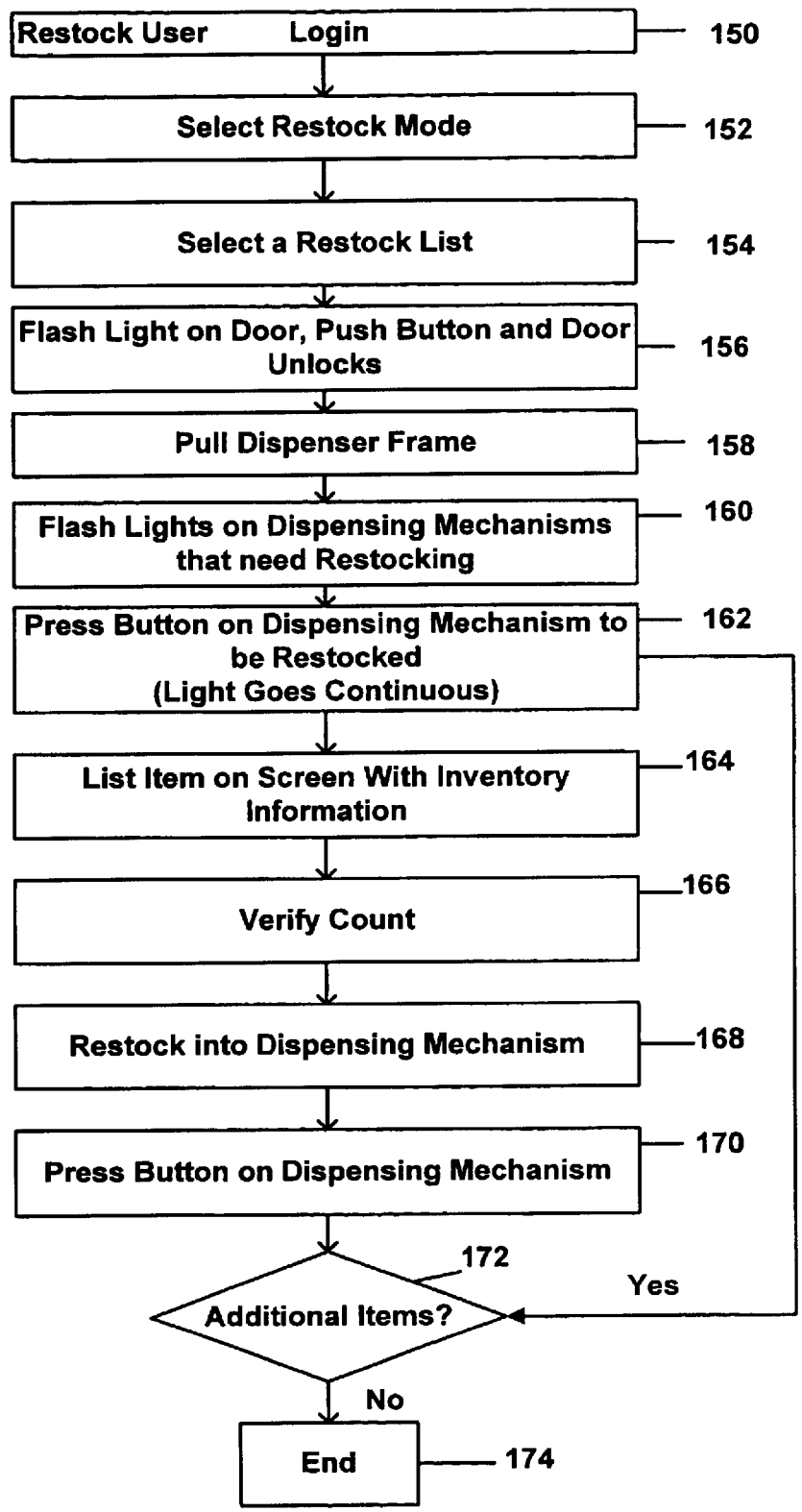
FIG. 9 is a flowchart illustrating one method for restocking items.

To restock dispensing cabinet 10, a restock technician logs into computer 30 as illustrated in step 150 of FIG. 9. A restock technician may be required to enter username and password information which is compared against a list of individuals that are authorized to access dispensing unit 42. If accepted, the restock technician may select the restock mode as illustrated in step 152. Computer 30 may have a record of all items stored in dispensing unit 42 along with their quantity. Further, computer 30 may include a restock list that was received from the pharmacy indicating which items are to be restocked, and may also include a quantity to restock. The restock technician may then select a restock list displayed on display screen 34 as illustrated in step 154.

Once a restock list has been selected, button 57 may light (and may optionally flash) to indicate to the restock technician where restocking should occur. Button 57 may be pressed which causes door 46 to unlock as illustrated in step 156. Door 46 may then be opened and dispenser frame 148 pulled out from dispensing unit 42 as illustrated in step 158. Conveniently, all lights 97 on dispensing mechanisms 50 that need to be restocked may flash to guide the restock technician to the dispensing mechanisms that need to be restocked as illustrated in step 160. The restock technician may then select one of the dispensing mechanisms to be restocked and press the associated button 96. This causes the associated light 97 to stop flashing and to continuously light as illustrated in step 162. Display screen 34 on computer 30 may also list the item that is associated with the dispensing mechanism that is being restocked as illustrated in step 164. Inventory information associated with the listed item may also be displayed on display screen 34. Optionally, the restock technician may be asked to verify the number of items within dispensing mechanism 50 as illustrated in step 166. To facilitate counting of the items, an "empty dispenser" icon may be selected on display screen 34, and one of the buttons 96 may be pressed to dispense all of the items. Hence, the restock technician may manually count the items in the dispensing mechanism and enter this information into computer 30. If needed, the quantity may be modified and stored in computer 30. In most cases, however, a count back will not be needed because the sensors detect when items have been dispensed. In cases where an item that was dispensed is not needed (such as when the patient is asleep), the item is still sensed, but may be returned to the side bin. As shown in step 168, the restock technician may then restock the items into dispensing mechanism 50 and enter the appropriate quantity. Button 96 may then be pressed to indicate that restocking of this dispensing mechanism is complete as illustrated in step 170. Conveniently, light 97 may then turn off to indicate restocking is complete. As shown in step 172, the restock technician may then determine whether additional dispensing mechanisms need to be restocked. If so, steps 162 through 170 are repeated. If not, the process ends at step 174. The restock technician may then push in dispenser frame 48 and close door 46 which then locks.

Hence, restocking may easily occur by simply withdrawing dispenser frame 48 to gain access to all of the dispensing mechanisms. Further, the restock technician is guided to the specific dispensing mechanisms that need restocking. Conveniently, computer 30 may be coupled to a network so that restocking information may conveniently downloaded to computer 30 (such as from a pharmacy) to facilitate the restocking process.

Figure 10:
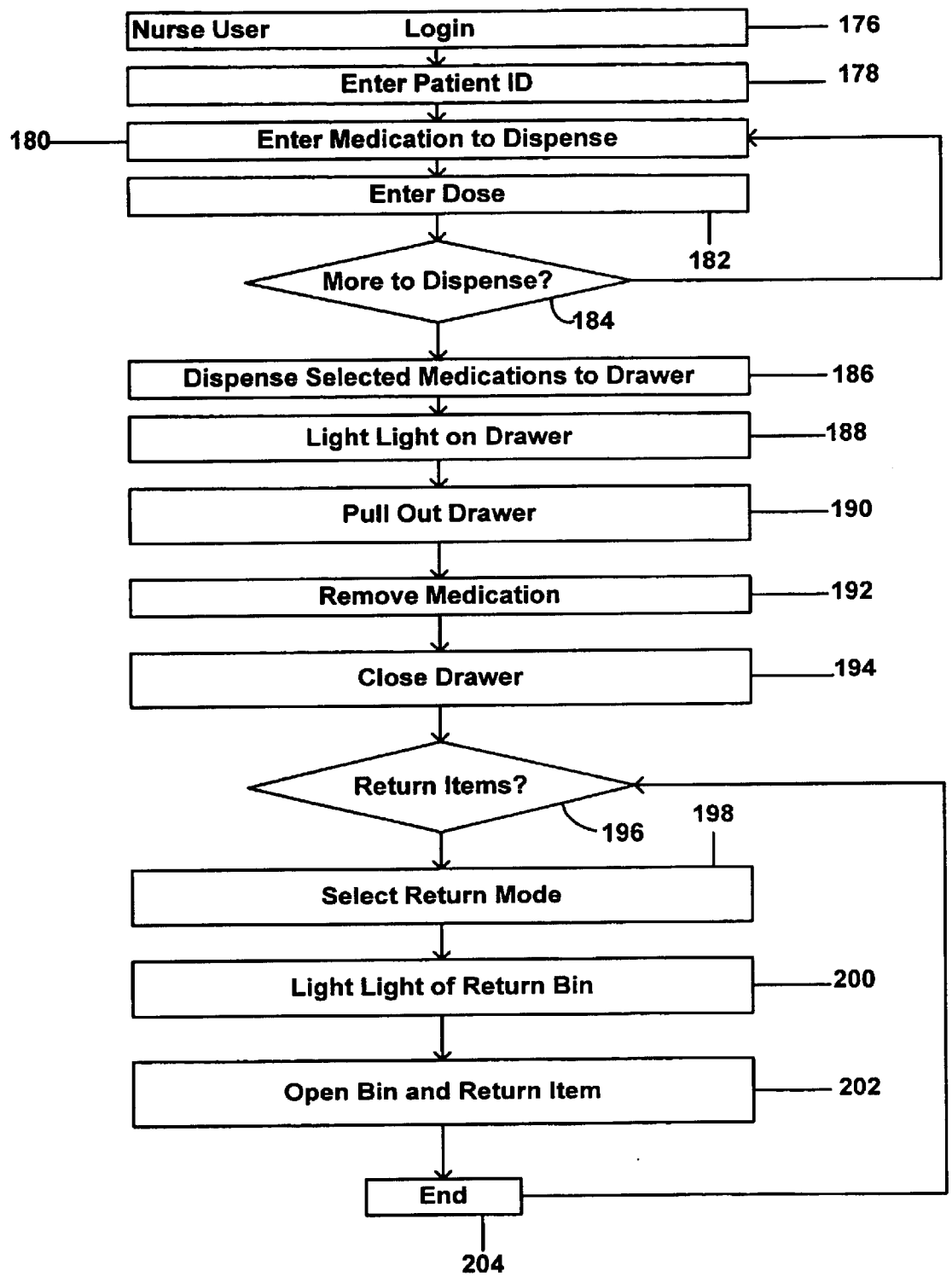
FIG. 10 is a flowchart illustrating one method for dispensing items.

FIG. 10 illustrates one exemplary method for dispensing items from dispensing unit 42 of cabinet 10. Initially, the nurse user logs into computer 30 as illustrated in step 176. This may require the nurse user to enter user name and password information to determine whether the nurse user may have access to the items stored in dispensing unit 42. As shown in step 178, a patient's identification information may also be entered. Computer 30 may then be placed into dispensing mode and the nurse user may enter a certain medication to be dispensed as illustrated in step 180. Conveniently, this medication may be selected from a list displayed on display screen 34. The nurse user may also be required to enter a dose as illustrated in step 182. Optionally, the nurse user may also be asked to verify the quantity to dispense. If the nurse user wishes to dispense more than one item, the process proceeds to step 184 where steps 180 and 182 may be repeated for each additional item. Once all items have been selected, the process proceeds to step 186.

In step 186, the appropriate dispensing mechanisms 50 dispense the appropriate number of medications which fall into dispense drawer 52. Conveniently, light 54 on dispense drawer 52 may light to indicate the dispense drawer having the dispensed items as shown in step 188. The nurse user may then pull out dispense drawer 52 as shown step 190 and remove the dispensed medication as illustrated in step 192. Finally, dispense drawer 52 is closed as shown in step 194.

In some circumstances, the nurse user may wish to return one or more items as illustrated in step 196. If so, the nurse user may select a return mode at computer 30 as illustrated in step 198. Light 62 on return unit 58 may then light to guide the nurse user to the appropriate location for returning the dispensed items as shown in step 200. Door 60 may then be opened and the item returned as illustrated in step 202. The process then ends at step 204.

The invention has now been described in detail for purposes of clarity and understanding. However, it will be appreciated that certain changes and modifications may be practiced within the scope of the appended claims.

What is claimed is:

1. A device for dispensing items, the device comprising:
   a cabinet having a front, a back, a pair of sides and an interior having a storage area;
   a dispenser frame operably coupled to the cabinet, wherein the dispenser frame includes a plurality of dividers;
   a plurality of dispensing mechanisms that are configured to hold a plurality of items within the storage area, wherein the dispensing mechanisms are operably coupled to the dispenser frame, and wherein the dividers are reconfigurable to permit the arrangement of the dispensing mechanisms to be adjusted;
   a divider sensing system associated with the dispenser frame to sense the configuration of the dividers;
   a visual indicator associated with each of the dispensing mechanisms;
   a lockable door coupled to the front of the cabinet so as to be positioned in front of the dispenser frame, wherein the door is operable to provide access to the interior of the cabinet and to the dispenser frame;
   a dispense drawer coupled to the cabinet below the storage area such that items dispensed from the dispensing mechanisms fall into the dispense drawer; and
   a computer that is operably coupled to the dispensing mechanisms and the visual indicators, wherein the computer is configured to actuate the visual indicators of the dispensing mechanisms that are to be restocked or modified, and wherein the computer is configured to store information on the configuration of the dividers.

2. A device as in claim 1, wherein the dispense drawer has a width that is essentially equal to the width of the dispenser frame, and wherein the dispenser frame is configured to be pulled out from the interior.

3. A device as in claim 2, wherein the dispense drawer extends across essentially the entire length of the front, and wherein the computer is configured to send a signal to automatically open the dispense drawer after an item is dispensed from one of the dispensing mechanisms.

4. A device as in claim 1, wherein the computer further includes a record of items stored in the cabinet, their quantity and their location.

5. A device as in claim 4, wherein the computer is configured to permit the selection of an item and to send a signal that is usable by one of the dispensing mechanisms to dispense the selected item.

6. A device as in claim 5, wherein the dispense drawer includes a light, and wherein the computer is configured to light the dispense drawer light upon selection of the item.

7. A device as in claim 4, wherein computer is configured to receive input on the items held within the dispensing mechanisms.

8. A device as in claim 7, wherein the dispensing mechanisms each include a sensor mechanism that is actuatable to send a signal to the computer when actuated.

9. A device as in claim 8, wherein the sensor mechanisms are each actuatable to indicate to the computer that the associated dispensing mechanism has been flagged to be assigned an item, and wherein the computer is configured to receive an input assigning an item to the flagged dispensing mechanism.

10. A device as in claim 8, wherein the sensor mechanisms are each actuatable to indicate to the computer that the associated dispensing mechanism is to be restocked.

11. A device as in claim 1, wherein the computer includes a record of individuals that may use the dispensing cabinet.

12. A device as in claim 11, wherein the computer is configured to unlock the door upon entry of appropriate identification information into the computer from an authorized individual.

13. A device as in claim 12, wherein the door includes a light, and wherein the computer is configured to light the door light upon receipt of a restocking request.

14. A device as in claim 13, wherein the visual indicators comprise lights, and wherein the computer is configured to light the light corresponding to each dispensing mechanism that is to be restocked.

15. A device as in claim 14, wherein the computer is configured to display the type of item to be restocked upon pressing of one of the lighted lights.

16. A device as in claim 15, wherein the computer is configured to produce a record of restocking and to turn off the light of the associated dispensing mechanism following restocking.

17. A device as in claim 1, wherein the dividers include connectors that are configured to interface with connectors on the dispensers.

18. A device as in claim 1, wherein the cabinet further includes a return unit that is adapted to receive returned items.

19. A device as in claim 1, further comprising a sensor system that is configured to detect when items fall from the dispensing mechanisms and into the dispense drawer.

20. A device as in claim 1, wherein the dispenser frame further includes a control circuit board that is electrically coupled to the computer and that is configured to be electrically coupled to the dispensing mechanisms.

21. A device as in claim 1, further comprising at least one holding drawer having multiple storage locations that are configured to hold additional items.

22. A device as in claim 1, further comprising at least one shelf having storage locations that are configured to hold additional items.

23. A method for configuring a dispensing device, the method comprising:
   providing a dispensing device comprising a cabinet having an interior; a dispenser frame coupled to the cabinet, wherein the dispenser frame includes a plurality of dividers for holding a plurality of dispensing mechanisms that each hold a plurality of items within the interior; a divider sensing system associated with the dispenser frame to sense the configuration of the dividers; a lockable door coupled to the front of the cabinet so as to be positioned in front of the dispenser frame; a dispense drawer coupled to the cabinet below the storage area such that items dispensed from the dispensing mechanisms fall into the dispense drawer; and a computer;

opening the door to access the dispenser frame;

arranging the dividers in a desired configuration;

providing a signal from the divider sensing system for supplying information on the arrangement of the dividers to the computer;

actuating a sensing mechanism that is associated with one of the dispensing mechanisms that is to be configured to generate a signal;

transmitting the signal to the computer to indicate that the dispensing mechanism that is associated with the actuated sensing mechanism is to be configured.

24. A method as in claim 23, further comprising entering into the computer an item to associate with the dispensing mechanism that is associated with the actuated sensing mechanism.

25. A method as in claim 23, further comprising restocking an item into the dispensing mechanism that is associated with the actuated sensing mechanism.

26. A method as in claim 23, wherein the sensing mechanism is actuated to enter an address of one of the dispensing mechanisms into the computer.

27. A method as in claim 26, wherein the address is determined by sensing the location of the new dispensing mechanism on the divider when the sensing mechanism is actuated.

28. A method as in claim 27, wherein the sensing mechanism comprises a button on the dispensing mechanism, and further comprising pressing the button on the dispensing mechanism to enter the address of the dispensing mechanism into the computer.

29. A method as in claim 24, wherein the item that is to be associated with the dispensing mechanism is entered by selecting an item from a list of items displayed by the computer.

30. A method as in claim 23, further comprising entering a request into the computer to dispense an item, and operating the dispensing mechanism to dispense the item into the dispense drawer.

* * * * *